United States Patent
Pratt et al.

(10) Patent No.: US 12,178,687 B2
(45) Date of Patent: Dec. 31, 2024

(54) METHOD AND SYSTEM FOR PROVIDING ACTIVE TISSUE SITE DEBRIDEMENT

(71) Applicant: Solventum Intellectual Properties Company, Maplewood, MN (US)

(72) Inventors: Benjamin A. Pratt, Wimborne (GB); Christopher B. Locke, Bournemouth (GB); James Seddon, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 1072 days.

(21) Appl. No.: 17/057,543

(22) PCT Filed: May 21, 2019

(86) PCT No.: PCT/US2019/033323
§ 371 (c)(1),
(2) Date: Nov. 20, 2020

(87) PCT Pub. No.: WO2019/226657
PCT Pub. Date: Nov. 28, 2019

(65) Prior Publication Data
US 2021/0186549 A1    Jun. 24, 2021

Related U.S. Application Data

(60) Provisional application No. 62/676,574, filed on May 25, 2018.

(51) Int. Cl.
*A61F 13/05* (2024.01)
*A61B 17/32* (2006.01)
(Continued)

(52) U.S. Cl.
CPC .............. *A61F 13/05* (2024.01); *A61B 17/32* (2013.01); *A61M 1/90* (2021.05); *A61M 1/915* (2021.05);
(Continued)

(58) Field of Classification Search
CPC .......... A61B 17/32; A61B 2017/00017; A61B 2017/00544; A61B 2017/00761;
(Continued)

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion in International Application No. PCT/US2019/033323, mailed on Aug. 23, 2019.

(Continued)

*Primary Examiner* — Benjamin J Klein

(57) ABSTRACT

A wound debridement system includes a wound dressing having an active layer (40) and a wound interface layer (10). The active layer is formed from one or more pneumatic members (45). The pneumatic members are arranged about a film layer (60), by which the pneumatic members are attached to the wound interface layer. A control unit (80) controls a drive unit (70) to intermittently apply pressure to the pneumatic members of the active layer. The pressure applied by the drive unit causes the pneumatic members to expand and contract. This movement of the pneumatic members is transferred to the wound interface layer, causing the wound interface layer to move relative to a tissue site to which the wound dressing is applied. The wound interface layer may be formed having an abrasive wound-facing (Continued)

surface, such that the movement of the wound interface layer causes a mechanical disruption and debridement of debris at the tissue site.

12 Claims, 7 Drawing Sheets

(51) Int. Cl.
*A61M 1/00* (2006.01)
*A61B 17/00* (2006.01)
*A61M 3/02* (2006.01)

(52) U.S. Cl.
CPC ............... *A61M 1/92* (2021.05); *A61M 1/96* (2021.05); *A61M 1/962* (2021.05); *A61B 2017/00017* (2013.01); *A61B 2017/00544* (2013.01); *A61B 2017/00761* (2013.01); *A61B 2017/320004* (2013.01); *A61M 1/75* (2021.05); *A61M 3/02* (2013.01)

(58) Field of Classification Search
CPC ....... A61B 2017/320004; A61B 2017/320008; A61F 13/00051; A61F 13/05; A61M 1/75; A61M 1/90; A61M 1/915; A61M 1/92; A61M 1/96; A61M 1/962; A61M 3/02; A61M 2205/05; A61M 2205/07; A61M 2205/106; A61M 2205/3576
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2011/0213319 A1 | 9/2011 | Blott et al. |
| 2015/0320603 A1 | 11/2015 | Locke et al. |
| 2017/0007752 A1 | 1/2017 | Freedman et al. |
| 2017/0209641 A1 | 7/2017 | Mercer et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |

(56) References Cited

FOREIGN PATENT DOCUMENTS

| | | |
|---|---|---|
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sept. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. ® Therapy Clinical Guidelines: A Reference Source for Clinicians; Jul. 2007.

METHOD AND SYSTEM FOR PROVIDING ACTIVE TISSUE SITE DEBRIDEMENT

CROSS-REFERENCE TO RELATED APPLICATIONS

This application claims the benefit of priority to international patent application number PCT/US2019/033323, filed on May 21, 2019, which claims the benefit of priority to U.S. Provisional Application No. 62/676,574, filed on May 25, 2018, the complete disclosures of which are hereby incorporated herein by reference in their entireties.

BACKGROUND

The present disclosure relates generally to tissue treatment systems, and more particularly, but without limitation, to a wound debridement system for active disruption and/or debridement of non-viable tissue at a tissue site without continual user intervention.

During treatment of a tissue site, such as, e.g. a wound site, debris may develop on or in the tissue site. In various embodiments, the debris may include biofilms, necrotic tissue, foreign bodies, eschar, lacerated tissue, devitalized tissue, contaminated tissue, damaged tissue, infected tissue, exudate, highly viscous exudate, fibrinous slough and/or other material. The debris may cover all or a portion of the tissue site.

The presence of debris in, on, or surrounding a tissue site may cause numerous problems. For example, debris that covers the tissue site may impair healing of the tissue site. Debris can also lower the effectiveness of beneficial tissue site treatments by preventing the treatments from reaching the tissue site. The presence of debris may also increase healing times and the risk of a more serious infection. Accordingly, in various embodiments, it may be desirable to disrupt the debris at a tissue site.

SUMMARY

One implementation of the present disclosure is an active debridement wound dressing including a wound interface layer and an active layer. The wound interface layer includes an abrasive surface configured to contact a wound and mechanically debride the wound when the wound interface layer moves relative to the wound. The active layer is coupled to the wound interface layer and includes a pneumatic structure configured to expand and collapse responsive to a pneumatic pressure applied to the active layer. The expansion and collapse of the pneumatic structure causes the wound interface layer to move relative to the wound and mechanically debride the wound.

In some embodiments, the active layer includes a fenestrated film fixed to the wound interface layer. The pneumatic structure includes a plurality of pneumatic segments fixed to the fenestrated film. In some embodiments, the pneumatic structure includes a central pneumatic hub and a plurality of radial segments extending radially outward from the central hub. In some embodiments, the pneumatic structure includes a pneumatic perimeter forming a closed shape around the central pneumatic hub and the plurality of radial segments. The plurality of radial segments connect the central pneumatic hub to the pneumatic perimeter.

In some embodiments, the pneumatic structure includes a plurality of pneumatic pathways that interconnect to form a honeycomb structure.

In some embodiments, a drape layer is sealable to a patient's skin surrounding the wound. The drape layer is configured to maintain the wound at negative pressure.

In some embodiments, the active layer is pneumatically coupled to the wound such that the pneumatic pressure applied to the active layer is substantially equivalent to a pressure at the wound. In some embodiments, the active layer is pneumatically isolated from the wound such that the pneumatic pressure applied to the active layer is different from a pressure at the wound.

In some embodiments, a first encapsulation layer and a second encapsulation layer encapsulate the active layer and pneumatically isolate the active layer from the wound. The first encapsulation layer is located on a first side of the active layer between the active layer and the wound interface layer. The second encapsulation layer is located on a second side of the active layer opposite the wound interface layer. A foam layer is coupled to the active layer opposite the wound interface layer such that the active layer is encapsulated between the foam layer and the wound interface layer.

In some embodiments, a control unit is coupled to the active layer and is configured to apply a positive or negative pneumatic pressure to the active layer. The control unit is configured to communicate with a driver unit outside the wound dressing and to apply the pneumatic pressure to the active layer upon receiving a control signal from the driver unit.

In some embodiments, the pneumatic structure is configured to collapse upon application of negative pressure to the active layer and return to a non-collapsed size or shape when the negative pressure is removed. In some embodiments, the pneumatic structure is configured to expand upon application of positive pressure to the active layer and return to a non-expanded size or shape when the positive pressure is removed. In some embodiments, the pneumatic structure is configured to oscillate between an expanded size or shape and a collapsed size or shape to impart oscillating movement to the wound interface layer.

One implementation of the present disclosure is an active debridement wound therapy system including a wound dressing and a therapy unit. The wound dressing includes a wound interface layer and an active layer. The wound interface layer includes an abrasive surface configured to contact a wound and mechanically debride the wound when the wound interface layer moves relative to the wound. The active layer is coupled to the wound interface layer and includes a pneumatic structure configured to expand and collapse responsive to a pneumatic pressure applied to the active layer, thereby causing the wound interface layer to move relative to the wound and mechanically debride the wound. The therapy unit is separate from the wound dressing and is configured to cause the pneumatic pressure to be applied to the active layer.

In some embodiments, the therapy unit includes a driver unit pneumatically coupled to the active layer via tubing and configured to apply the pneumatic pressure to the active layer via the tubing. In some embodiments, the wound dressing includes a control unit coupled to the active layer and configured to communicate with the therapy unit. The control unit is configured to apply the pneumatic pressure to the active layer upon receiving a control signal from the therapy unit.

In some embodiments, the active layer includes a fenestrated film fixed to the wound interface layer. The pneumatic structure includes a plurality of pneumatic segments fixed to the fenestrated film.

In some embodiments, the pneumatic structure includes a central pneumatic hub and a plurality of radial segments extending radially outward from the central hub.

In some embodiments, the pneumatic structure includes a pneumatic perimeter forming a closed shape around the central pneumatic hub and the plurality of radial segments. The plurality of radial segments connect the central pneumatic hub to the pneumatic perimeter.

In some embodiments, the pneumatic structure includes a plurality of pneumatic pathways that interconnect to form a honeycomb structure.

In some embodiments, the wound dressing further includes a drape layer sealable to a patient's skin surrounding the wound and configured to maintain the wound at negative pressure.

In some embodiments, the active layer is pneumatically coupled to the wound such that the pneumatic pressure applied to the active layer is substantially equivalent to a pressure at the wound. In some embodiments, the active layer is pneumatically isolated from the wound such that the pneumatic pressure applied to the active layer is different from a pressure at the wound.

In some embodiments, the wound dressing further includes a first encapsulation layer and a second encapsulation layer encapsulating the active layer and pneumatically isolating the active layer from the wound. The first encapsulation layer is located on a first side of the active layer between the active layer and the wound interface layer. The second encapsulation layer is located on a second side of the active layer opposite the wound interface layer. The wound dressing further includes a foam layer coupled to the active layer opposite the wound interface layer such that the active layer is encapsulated between the foam layer and the wound interface layer.

In some embodiments, the pneumatic structure is configured to collapse upon application of negative pressure to the active layer and return to a non-collapsed size or shape when the negative pressure is removed. In some embodiments, the pneumatic structure is configured to expand upon application of positive pressure to the active layer and return to a non-expanded size or shape when the positive pressure is removed. In some embodiments, the pneumatic structure is configured to oscillate between an expanded size or shape and a collapsed size or shape to impart oscillating movement to the wound interface layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring to FIGS. 1-6, various embodiments of an active wound debridement system 1 configured to disrupt areas of debris 7 at a tissue site 5, such as, e.g. a wound site, are shown. The active wound debridement system 1 is configured to provide continued, active mechanical debridement of debris 7 at the tissue site 5 without requiring any additional user skill or effort to operate the wound debridement system 1 other than what would be required to apply and activate an existing negative pressure wound therapy ("NPWT") system, such as e.g. a V.A.C.® therapy unit as available from Kinetic Concepts, Inc. (KCI) of San Antonio, Tex.

Figure 1:
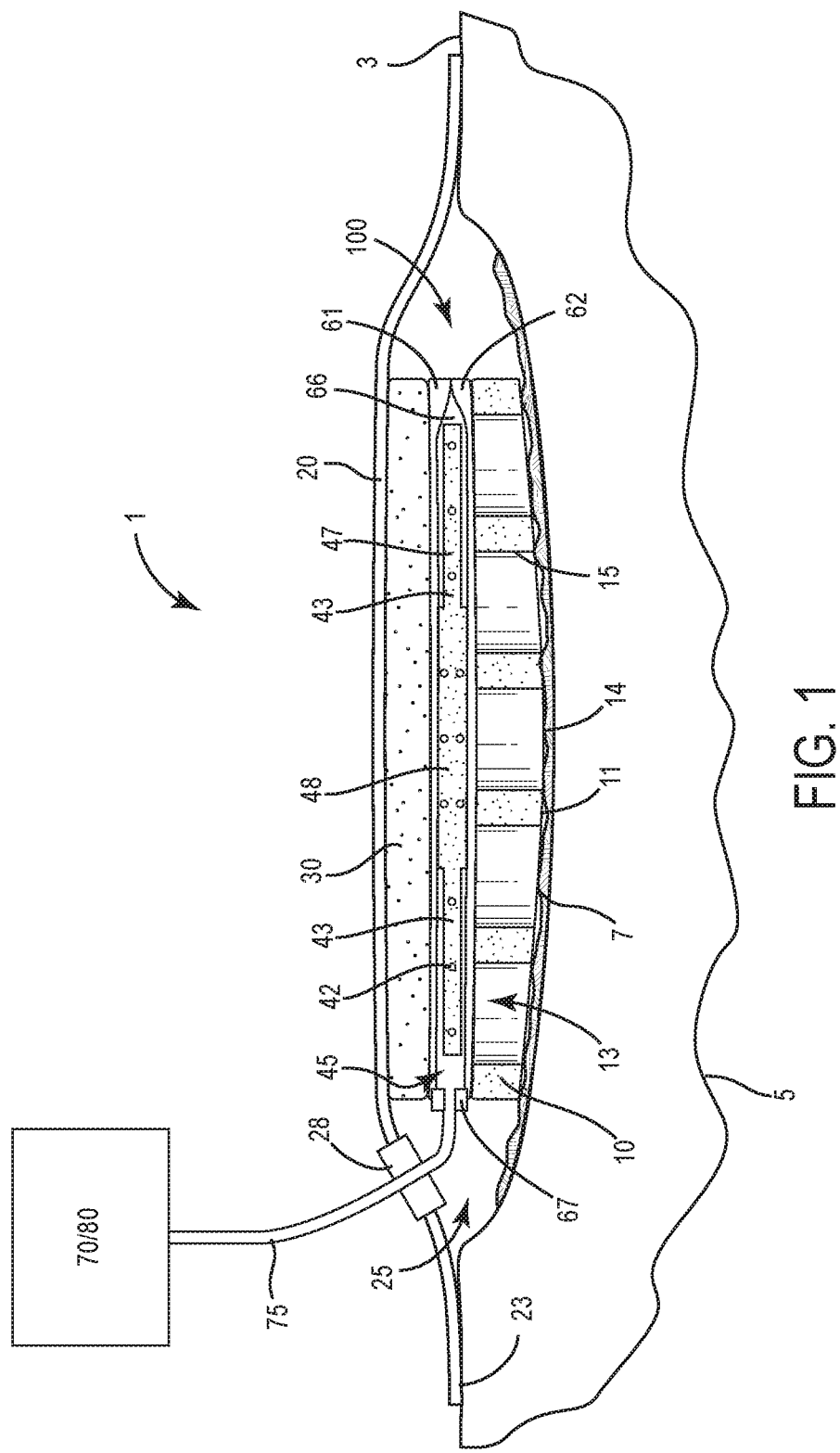
FIG. 1 is a cross-sectional side view of an active wound debridement system applied to a tissue site, according to an exemplary embodiment.

As shown in FIG. 1, the wound debridement system 1 generally comprises an active debridement wound dressing 100, a drape layer 20 configured to position the wound dressing 100 at a desired tissue site 5, a drive unit 70 adapted to activate the active layer 40 and thereby drive the wound interface layer 10 relative to the tissue site 5, and a control unit 80 adapted to control the delivery of pressure by the drive unit 70 to the active layer 40.

During operation of the wound debridement system 1, the wound dressing 100 is positioned on or within a desired tissue site 5. Once positioned, the wound dressing 100 is secured to the patient's skin 3 using the drape layer 20. Depending on whether the active layer 40 is intended to be driven by non-localized or isolated changes in pressure, the drape layer 20 may be applied to the patient's skin 3 so as to form a sealed, substantially fluid-tight treatment space 25 surrounding the tissue site 5 and the wound dressing 100.

The control unit 80 may then be operated to control the application of pressure by the drive unit 70 to the active layer 40 of the wound dressing 100. The pressure applied by the drive unit 70 is configured to cause the cyclical, alternating or intermittent collapse and expansion of the one or more pneumatic members 45 forming the active layer 40. The oscillation of the pneumatic members 45 between a collapsed and an expanded state drives the wound interface layer 10, such that the wound interface layer 10 is translated relative to the tissue site 5. This movement of the wound interface layer 10 relative to the tissue site 5 acts to mechanically disrupt and debride debris 7 located at the tissue site 5.

Figure 6:
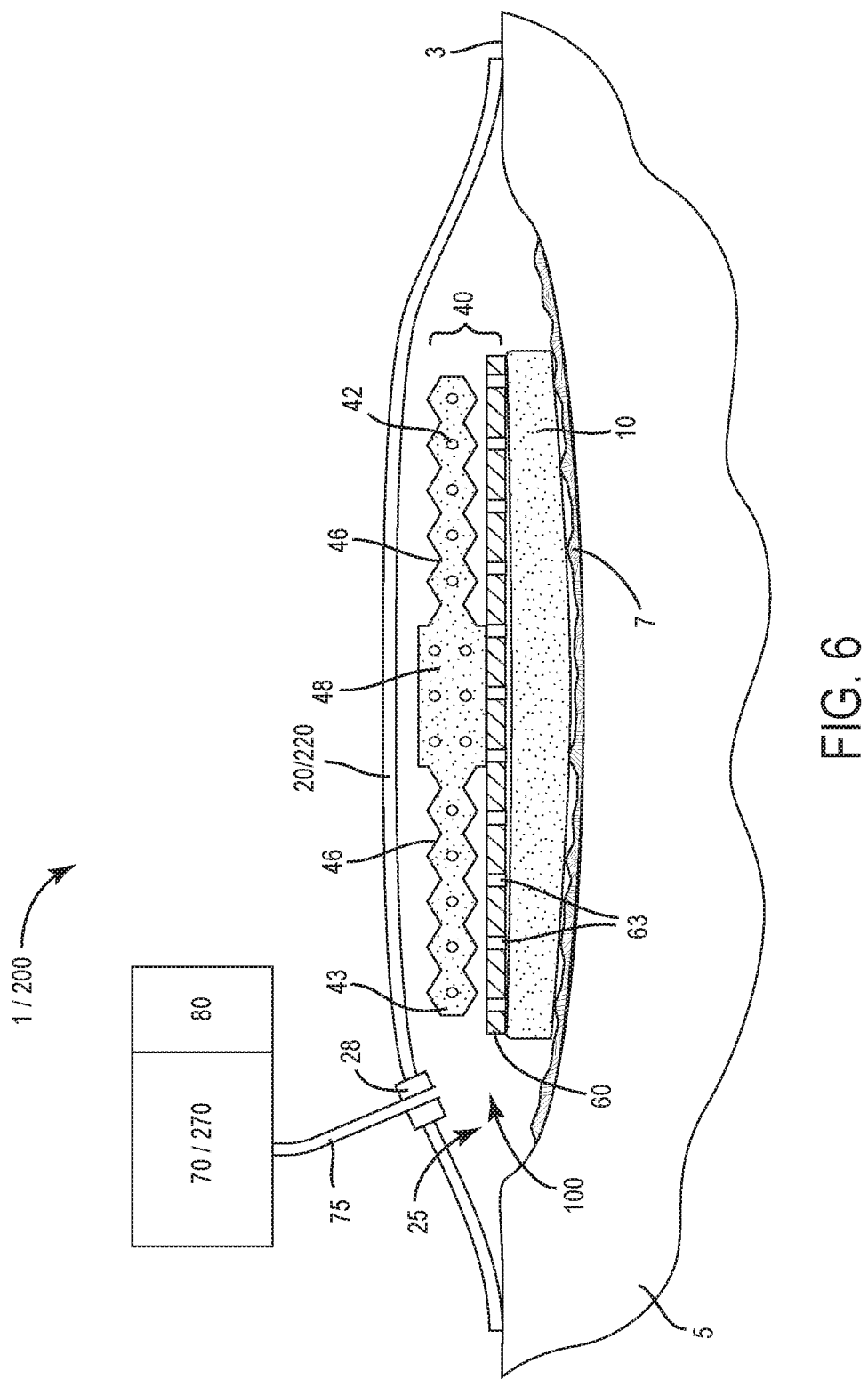
FIG. 6 is a cross-sectional side view of an active wound debridement system applied to a tissue site being used in conjunction with a negative pressure wound therapy system, according to an exemplary embodiment.

In some embodiments, the wound debridement system 1 may be used in conjunction with, or form a part of, an additional therapeutic treatment system configured to provide additional therapeutic treatment to the tissue site 5 to which the wound debridement system 1 is applied. For example, as illustrated in FIG. 6, in some embodiments, the wound debridement system 1 may be incorporated into and be used in conjunction with a NPWT system 200.

Wound Dressing

In general, the wound dressing 100 includes a wound interface layer 10 configured to provide mechanical movement which disrupts debris 7 at a tissue site 5 and an active layer 40 configured to drive the movement of the wound interface layer 10. An absorbent layer 30 may optionally also be incorporated into the wound dressing 100.

The wound dressing 100 may be substantially planar or may be contoured for application to body surfaces having high curvature. The size of wound dressing 100 can vary depending on the size of the tissue site 5 to be treated. For example, it is contemplated that the size of wound dressing 100 can be within a range of approximately 50 cm$^2$ to approximately 3000 cm$^2$, and more preferably within a range of approximately 300 cm$^2$ to approximately 800 cm$^2$. However, other shapes and sizes of wound dressing 100 are also possible depending on intended use.

i. Wound Interface Layer

The wound interface layer 10 is adapted to contact a tissue site 5 along a lower, wound-facing surface 11 of the wound interface layer 10 to mechanically debride debris 7 at the tissue site 5 upon movement of the wound interface layer 10 relative to the tissue site 5. Although the wound interface layer 10 is shown as having a generally rounded rectangular shape, the wound interface layer 10 may be formed having any number of, and combination of, sizes, shapes, and/or thicknesses depending on a variety of factors, such as, e.g. the type of treatment being implemented or the nature and size of the tissue site 5 being treated, etc.

Additionally, the size and shape of the wound interface layer 10 may be selected to accommodate the type of tissue site 5 being treated and the degree of contact (e.g. full or partial contact) desired between the tissue site 5 and the wound interface layer 10. For example, if the tissue site 5 is a wound, the shape, size and thickness of the wound interface layer 10 may vary depending on whether the wound interface layer 10 is intended to partially or completely fill the wound, or if the wound interface layer 10 is intended to only be placed over the wound. If the wound interface layer 10 is intended to partially or completely fill the wound, the size and shape of the wound interface layer 10 may be adapted to the contours of the wound.

Any number of bio-compatible materials may be used to construct the wound interface layer 10. A non-limiting, non-exhaustive list of the various materials that may be used to form the wound interface layer 10 may include: bioresorbable materials; materials configured to serve as a scaffold for new cell-growth, such as, e.g. calcium phosphate, collagen, PLA/PGA, coral hydroxy apatites, carbonates, or processed allograft materials; thermoplastic elastomers; 3D textiles, also referred to as a spacer fabric, such as the 3D textiles produced by Heathcoat Fabrics, Ltd., Baltex, and Mueller Textil Group; foam, such as e.g. GranuFoam®, V.A.C. VeraFlo® foam, or V.A.C. WhiteFoam®, each available from Kinetic Concepts, Inc. of San Antonio, Texas; etc.

The materials used to form the wound interface layer 10, the properties of the wound-facing surface 11 and/or the configuration and structure of the wound-facing surface 11 may be selected to enhance the ability of the wound interface layer 10 to disrupt debris 7 at the tissue site 5. For example, in some embodiments, the wound-facing surface 11 may be formed of an abrasive material. In other embodiments, the wound-facing surface 11 may be defined by a textured surface having an uneven, coarse, or jagged profile that can induce strains and stresses at the tissue site 5. In such embodiments, the wound-facing layer may be formed of an abrasive or non-abrasive material. In yet other embodiments, the wound interface layer 10 may be formed of an abrasive or non-abrasive compressible material, with the compression of the compressible material being adapted to increase the amount by which the wound-facing surface 11 is translated or oscillated in a lateral and/or longitudinal direction relative to the tissue site 5 during treatment.

Figure 3:
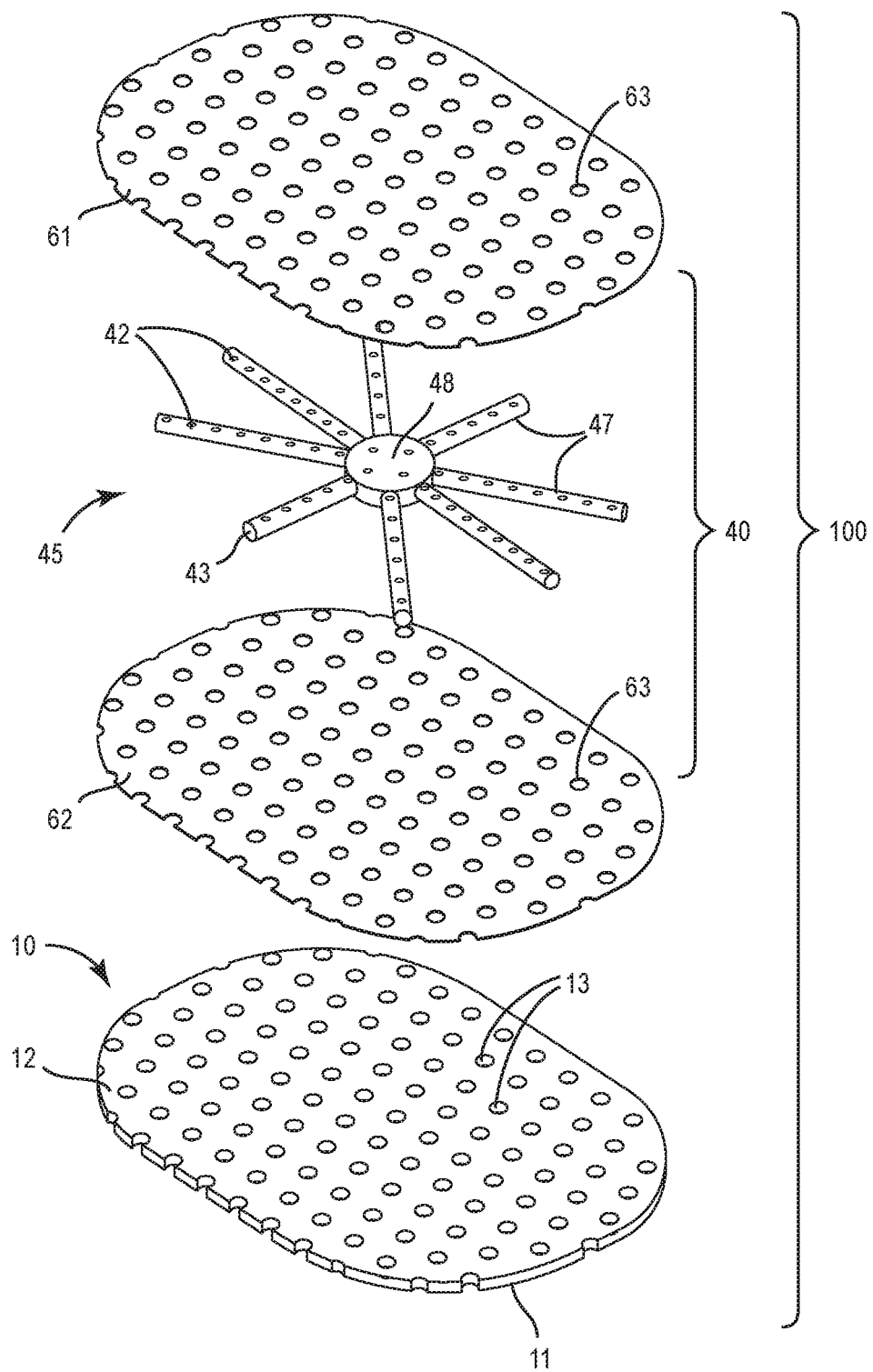
FIG. 3 is an exploded top perspective view of a wound dressing according to an exemplary embodiment.
Figure 4:
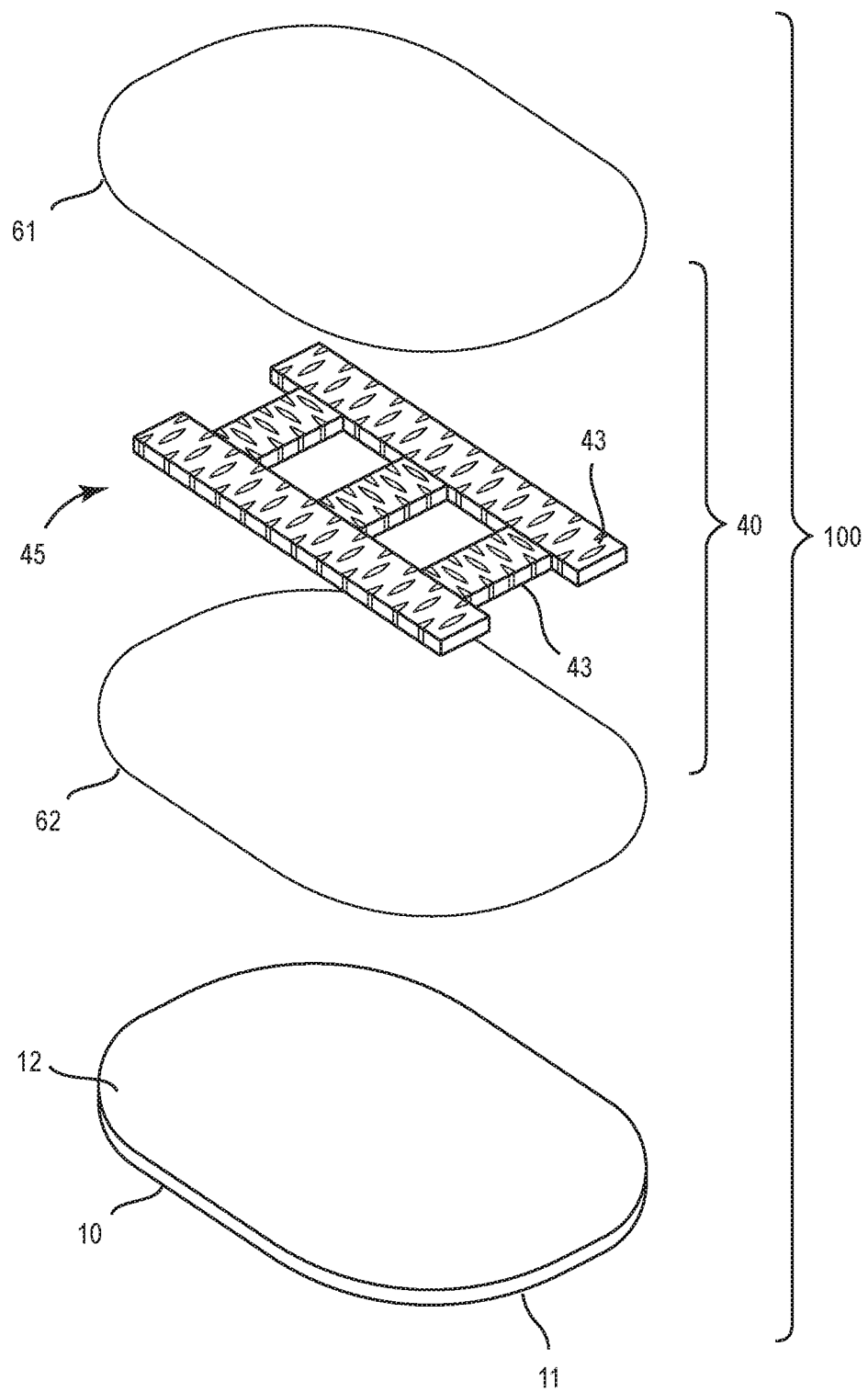
FIG. 4 is an exploded top perspective view of a wound dressing according to an exemplary embodiment.

As illustrated in FIG. 4, in various embodiments the wound-facing surface 11 of wound interface layer 10 may be formed having a generally solid, continuous, uninterrupted surface. In other embodiments, the ability of the wound interface layer 10 to disrupt debris 7 at the tissue site 5 may be enhanced via the selective removal of areas or portions of the wound-facing surface 11. For example, as illustrated in FIG. 3, in one embodiment, the wound interface layer 10 may be constructed with a plurality of perforations or through-holes 13 extending entirely or partially through the wound interface layer 10 from the wound-facing surface 11 to an upper surface 12 of the wound interface layer 10.

The dimensions of the through-holes 13 may be varied as desired. While in some embodiments each of the through-holes 13 may have identical dimensions, in other embodiments the through-holes 13 may be formed having varied dimensions. Regardless of the dimensions selected for the through-holes 13, in embodiments in which the wound interface layer 10 is formed from a foam-like or other porous material, it is to be understood that the through-holes 13 do not include the pores of the material forming the wound interface layer 10, but rather are discrete perforations formed through the material forming the wound interface layer 10.

The through-holes 13 may be arranged about the wound interface layer 10 in any number of desired arrangements or patterns, including a random arrangement of the through-holes 13 about the wound interface layer 10. As illustrated in FIG. 3, in some embodiments, the through-holes 13 may be arranged linearly, with adjacent rows of through-holes 13 optionally being offset from one another.

As shown in FIG. 3, in some embodiments, the through-holes 13 may have a circular shape. In other embodiments, the through-holes 13 may be formed having any number of other shapes, or any combination of different shapes, including, e.g. hexagonal, ovoid, or triangular shapes. When contracted, through-holes 13 having different cross-sectional shapes may generate and distribute concentrated stresses in different dimensions, and may accordingly influence disruption of debris 7 in different ways. As such, in various embodiments the cross-sectional shape of the through-holes 13 may be based on the tissue site 5 being treated and/or the degree of abrasion that may be desired at the tissue site 5.

Regardless of the shape, size, arrangement, or degree to which the through-holes 13 extend through the wound interface layer 10, the through-holes 13 formed in the wound interface layer 10 define void spaces in the wound-facing surface 11. In response to the wound interface layer 10 being subjected to negative pressure and/or being compressed, the voids provide spaces into which the wound-facing surface 11 is laterally and/or longitudinally collapsed. As the wound-facing surface 11 is compressed from its initial, relaxed configuration into the spaces defined by the voids, the lateral and/or longitudinal translation of the wound-facing surface 11 relative to the tissue site 5 concentrates a shear force on the tissue site 5 that allows for the disruption of the debris 7 at the tissue site 5.

The disruption of the debris 7 at the tissue site 5 may also be augmented by the localization of forces along the edges 14 of the through-holes 13 during the application of negative pressure to and/or the compression of the wound interface layer 10, which may result in the edges 14 acting as cutting surfaces that disrupt debris 7 at the tissue site 5. Additionally, in some embodiments, during the application of negative pressure and/or as a result of the compression of the wound interface layer 10, debris 7 may become trapped within the voids as the through-holes 13 collapse. Forces concentrated by the inner vertical surfaces 15 of the walls of the through-holes 13 on this trapped debris 7 may act to provide additional disruption of the debris 7 at the tissue site 5.

Figure 2A:
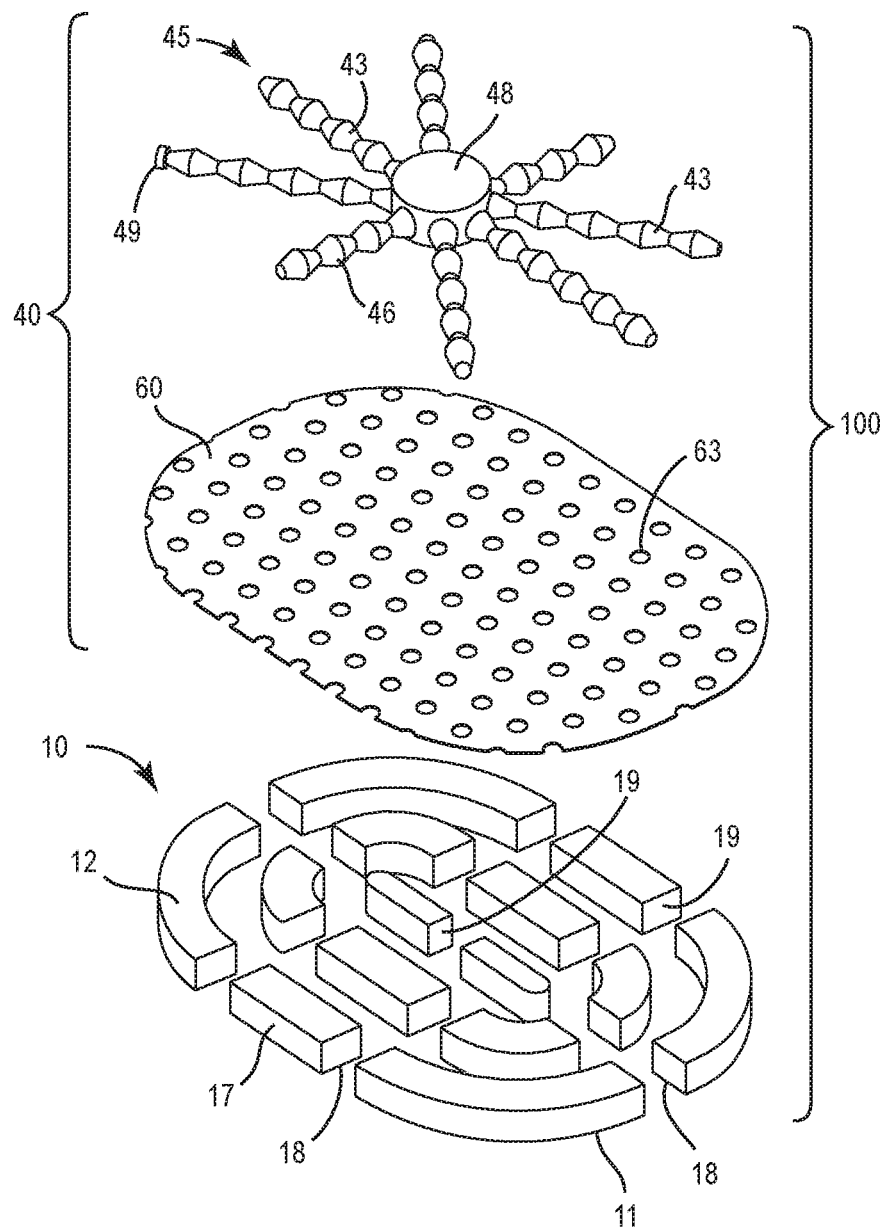
FIG. 2A is an exploded top perspective view of a wound dressing, according to an exemplary embodiment.
Figure 5:
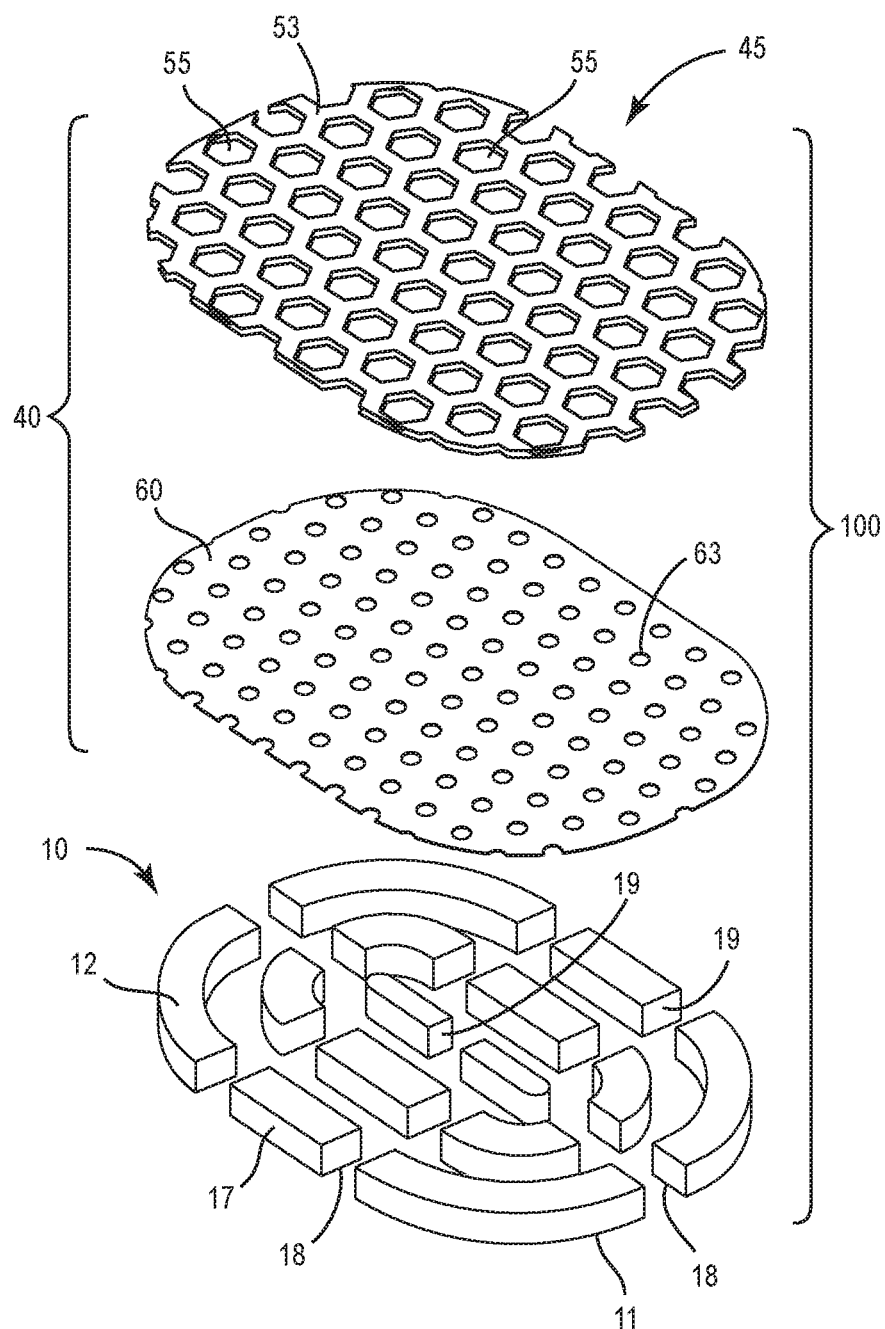
FIG. 5 is an exploded top perspective view of a wound dressing according to an exemplary embodiment.

As illustrated in FIGS. 2A and 5, in some embodiments, the selective removal of areas or portions of the wound interface layer 10 may be provided in the form of the wound interface layer 10 being formed of a plurality of discrete or connected segments 17. In an initial configuration—prior to the application of negative pressure and/or the compression of the wound interface layer 10—the segments may be arranged and spaced relative to one another with voids separating adjacent segments 17, such that the wound-facing surface 11 of the wound interface layer 10 is defined by a non-solid, interrupted surface. The segments 17 may be arranged relative to one another such that, upon negative pressure being applied to and/or compression of the wound interface layer 10, the segments 17 collapse inwards to form a substantially solid, compact surface defined by the inter-fitted arrangement of adjacent segments 17 with one another.

The effect of the contraction of the segments 17 of wound interface layer 10 embodiments such as those illustrated in, e.g. FIGS. 2A and 5, is similar to the effect of the contraction and collapse of through-holes 13 of wound interface layer 10 embodiments such as that illustrated in, e.g. FIG. 3. In particular, the translation of the segments 17 relative to the tissue site 5 in a lateral and/or longitudinal direction concentrates a shear force on the tissue site 5 as the segments 17 are collapsed and translated into the inter-fitted, compressed segment 17 configuration illustrated in, e.g. FIG. 2C. Also, concentrated forces imparted by the edges 18 of segments 17 on the debris as well as forces imparted by the vertical surfaces 19 of segments 17 on debris 7 that becomes trapped between adjacent segments 17 as the wound interface layer 10 collapses assist in the debridement of debris 7 at the tissue site 5.

Although embodiments of the wound interface layer 10 formed with through-holes 13 or segments 17 each assist in tissue site 5 debridement, in various embodiments, the larger wound-facing surface 11 surface area, the greater amount of defined edges 18, and the greater total surface area defined by vertical surfaces 15 characterizing embodiments of the wound interface layer 10 having segments 17 (such as e.g. illustrated in FIGS. 2A and 5) may allow for a greater degree of debris 7 disruption as compared to embodiments of the wound interface layer 10 formed with through-holes 13 (such as e.g. illustrated in FIG. 3).

In the wound interface layer 10 embodiments formed with through-hole 13 or segment 17 illustrated in FIGS. 3 and 5, respectively, the through-holes 13 and segments 17 are illustrated as defining voids in the wound-facing surface 11 when the wound interface layer 10 is in an initial configuration, and as being adapted to collapse into a compressed configuration upon the application of negative pressure. However, it is to be understood that, in other embodiments, the wound surface layer 10 may be configured such that, in an initial configuration the wound-interface surface 11 defines a substantially continuous, solid surface, with the wound surface layer 10 being adapted to transition into an expanded configuration having voids defined by through-holes 13 and/or segments 17 upon the application of positive pressure to the wound interface layer 10.

ii. Active Layer

Active layer 40 is configured to intentionally oscillate, translate, collapse, or otherwise move the wound interface layer 10 such that unhealthily tissue or other debris 7 may be debrided from the tissue site 5. The active layer 40 generally comprises one or more pneumatic members 45 that may be operably coupled to the wound interface layer 10 via an interconnection, such as, e.g. film layer 60. The one or more pneumatic members 45 are configured to expand and collapse responsive to a pneumatic pressure applied to the active layer 40 by a drive unit 70.

a. Pneumatic Members

The transition of the pneumatic members 45 of the active layer 40 between an expanded and collapsed configuration is adapted to impart a translational and/or oscillating movement to the wound interface layer 10. The design of and the materials used to the form pneumatic members 45 are adapted to allow the pneumatic members 45 to collapse and expand in response to changes in pressure applied by the drive unit 70.

In some embodiments, the pneumatic members 45 may be configured to collapse upon application of negative pressure and return to a non-collapsed configuration when the negative pressure is removed. In other embodiments, the pneumatic members 45 may be configured to expand upon application of positive pressure and return to a non-expanded configuration when the positive pressure is removed. In some embodiments, the pneumatic members 45 may include a combination of pneumatic members 45 configured to collapse from an initial expanded configuration upon application of negative pressure and pneumatic members 45 configured to expand from an initial compressed configuration upon application of positive pressure.

In embodiments in which the drive unit 70 is adapted to apply both negative and positive pressure to drive the active layer 40, the pneumatic members 45 may be formed without being biased to either an expanded or collapsed position, with the cyclical application of positive and negative pressure causing the pneumatic members 45 to transition from an expanded to a collapsed state.

Generally, the pneumatic members 45 are adapted to be highly compressible, allowing the active layer 40 to easily collapse and expand. The rigidity of the materials selected to form the pneumatic members 45 may be used as one way to control the rate of oscillation and/or the degree of translation that will be imparted onto the wound interface layer 10 by the active layer 40.

The pneumatic members 45 may be configured to collapse in one, all, or a combination of the lateral, longitudinal, and/or vertical directions. For example, in various embodiments, the pneumatic members 45 may be configured to collapse in only the lateral and longitudinal directions in response to changes in pressure. In other embodiments, the pneumatic members 45 may be adapted to allow for collapse along only a single direction.

1. Single Direction Collapsible Structures

As illustrated in FIGS. 2-4, in various embodiments, the one or more pneumatic members 45 of the active layer 40 may comprise one or more single-direction collapsible structures 43 designed to collapse in a single direction, such as, e.g. along a longitudinal axis of the pneumatic member 45. The single-direction collapsible structures 43 may be centered about and extend generally uniformly (i.e. in a linear manner) or may extend non-linearly (e.g. along a curve) with respect to the axis the single-direction collapsible structures 43 are configured to collapse along (e.g. the longitudinal axis).

As will be discussed in more detail below, when arranged with other single-direction collapsible structures 43 to form the active layer 40, the arrangement of the single-direction collapsible structure 43 may allow for movement of the active layer 40 in more than one direction, even though each individual single-direction collapsible structure 43 forming the active layer 40 is configured to only collapse and expand along a single direction.

The single-direction collapsible structures 43 may be designed to expand from an initial, collapsed state upon the application of positive pressure, and automatically retract to their initial configuration when the positive pressure is removed. Alternatively, the single-direction collapsible structures 43 may be designed to collapse from an initial, expanded state upon the application of negative pressure, returning to their initial configuration once the negative pressure is removed.

Referring to FIGS. 2-4, the single-direction collapsible structures 43 may be formed having any number of configurations, and may be formed of any number of materials that allow the single-direction collapsible structures 43 to collapse and expand in a single direction in response to changes in pressure. In some embodiments, such as e.g. illustrated in FIGS. 2A and 3, the single-direction collapsible structures 43 may be formed having a hollow interior 41, with one or more apertures 42 optionally being provided about an exterior of the single-direction collapsible structure 43 to provide for fluid communication between the hollow interior 41 and the ambient environment. In other embodiments, such as, e.g. shown in FIG. 4, the single-direction collapsible structures 43 may define a substantially solid structure, formed without a hollow interior 41.

Figure 2B:
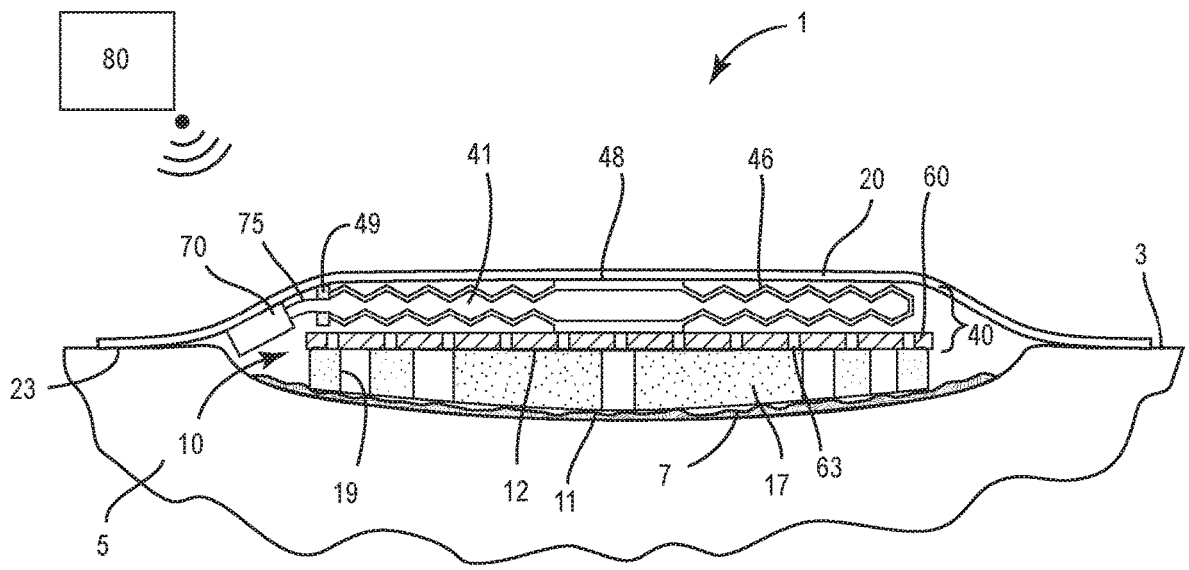
FIG. 2B is a cross-sectional side view of an active wound debridement system incorporating the wound dressing of FIG. 2A applied to a tissue site, the wound dressing being shown in an initial, expanded configuration, according to an exemplary embodiment.
Figure 2C:
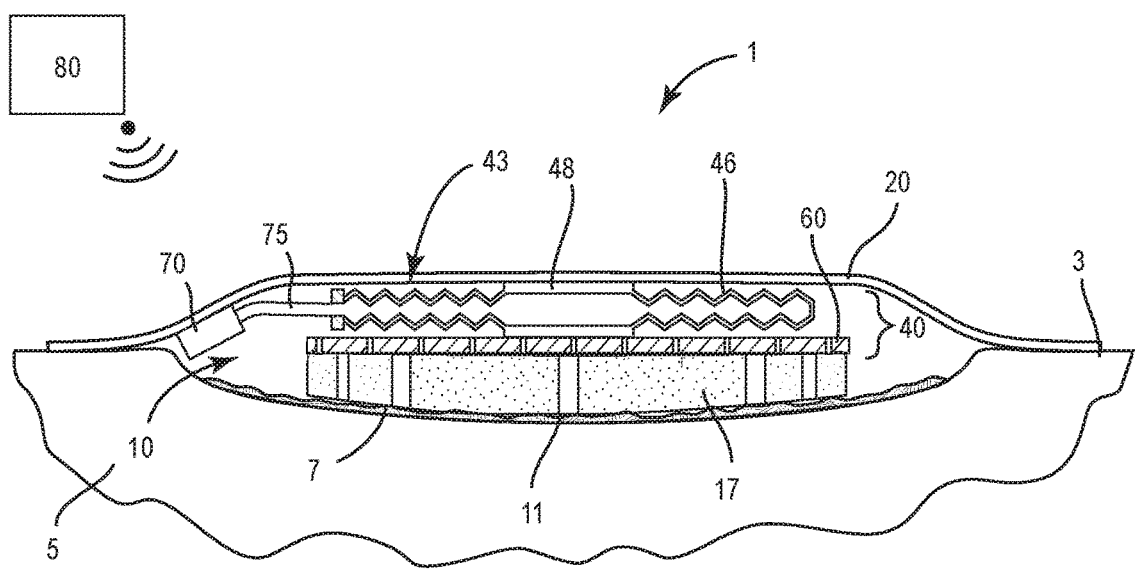
FIG. 2C is a cross-sectional side view of the active wound debridement system of FIG. 2B after the application of negative pressure to the active layer of the wound dressing, according to an exemplary embodiment.

As shown in FIGS. 2A-2C, in some embodiments the single-direction collapsible structures 43 may be formed as bellows 46 made, e.g., from molded plastic. The folded arrangement of the bellows 46 may advantageously allow for significant extension/contraction of the single-direction collapsible structures 43, thereby allowing the active layer 40 to induce a significant amount of lateral and/or longitudinal translation and/or oscillation of the wound interface layer 10 relative to the tissue site 5. In such embodiments, the configuration of and/or dimensions of the bellows 46 may be varied depending on the degree of movement of the wound interface layer 10 that is desired.

In some embodiments, such as illustrated e.g. in FIG. 3, the single-direction collapsible structures 43 may be formed of thin-walled collapsible tubes 47. As shown in FIG. 3, in some embodiments, the thin-walled collapsible tubes 47 forming the single-direction collapsible structures 43 may be arranged in a hub and spoke arrangement. In other embodiments, the thin-walled collapsible tubes 47 forming the single-direction collapsible structures 43 may be arranged in any other number of configurations that would allow for radial contraction and expansion of the active layer and/or contraction and expansion of the active layer 40 in any other desired direction.

In other embodiments, such as, e.g. shown in FIG. 4, the single-direction collapsible structures 43 may be formed from a compressible material, such as, e.g. an open-cell foam, with the materials and hole patterns defining the compressible material being adapted to allow for only unidirectional collapse and expansion. In yet another embodiment (not shown), the single-direction collapsible structures 43 may be formed of a network of hollow or solid, articulated, non-compressible segments that are configured to collapse and expand in an accordion-like manner.

The one or more single-direction collapsible structures 43 may be spaced and positioned about the active layer 40 in any desired pattern, design or arrangement. Although the single-direction collapsible structures 43 are themselves individually adapted to collapse and expand along a single direction, the arrangement of the single-direction collapsible structures 43 about the active layer 40 may allow for either uni- or multi-directional movement of the active layer 40. Accordingly, in various embodiments, the configuration, arrangement and/or positioning of the single-direction collapsible structures 43 about the active layer 40 may be based on the direction and/or degree of movement of the wound interface layer 10 that is desired. In some embodiments, such as, e.g. illustrated in FIGS. 2-4, the single-direction collapsible structures 43 may be arranged such the single-direction collapsible structures 43 collapse inwards towards a center of the wound dressing 100 upon the application of negative pressure.

The pattern, design and arrangement of the single-direction collapsible structures 43 about the active layer 40 may define a pneumatic member 45 formed of a plurality of discretely positioned single-direction collapsible structures 43, or may define a pneumatic member 45 formed of a plurality of single-direction collapsible structures 43 forming a single, unitary structure having a desired pattern and design. While in some embodiments the one or more single-direction collapsible structures 43 may be arranged uniformly and/or symmetrically about the active layer 40, in other embodiments the single-direction collapsible structures 43 may be positioned randomly about the active layer 40.

As illustrated by FIGS. 2-4, in some embodiments, a plurality of radially outwardly extending single-direction collapsible structures 43 may be arranged to form a unitary, spoke-like pneumatic member 45, with the inwardly located ends of the single-direction collapsible structures 43 optionally being attached to and extending outwards from a centrally located anchor point or hub 48. In some embodiments, a single-direction collapsible structure extending continuously or interruptedly about a perimeter of the active layer 40 may optionally be attached to and be in fluid, pneumatic communication with the outwardly located ends of the single-direction collapsible structures 43 defining the spoke-like pneumatic member 45. In addition to assisting in the expansion and contraction of the active layer 40, the inclusion of one or more single-direction collapsible structures 43 forming an outer ring surrounding the periphery of the hub and spoke assembly may also facilitate the manufacture and assembly of the active layer 40.

In embodiments in which the pneumatic member 45 is formed of a plurality of single-direction collapsible structures 43 having hollow interiors 41, such as, e.g. illustrated by FIGS. 2A-2C, the hollow interiors 41 of some or all of the single-direction collapsible structures 43 may be fluidly (i.e. pneumatically) connected. In other embodiments, the hollow interiors 41 of some or all of the single-direction collapsible structures 43 may be fluidly (i.e. pneumatically) isolated from adjacent hollow interior 41 single-direction collapsible structures 43.

In embodiments in which discrete, non-interconnected single-direction collapsible structures 43 having hollow interiors 41 form the active layer 40, each of the discrete, non-interconnected single-direction collapsible structures 43 may be formed with one or more apertures 42 configured to allow for fluid communication between the hollow interior 41 of the single-direction collapsible structure 43 and the external environment. The apertures 42 are adapted to allow for changes in pressure external to the single-direction collapsible structure 43 to be transferred to the hollow interior 41 of the single-direction collapsible structure 43, with the resultant change in pressure in the hollow interior 41 of the single-direction collapsible structure 43 adapted to cause the collapse or expansion of the single-direction collapsible structure 43.

In embodiments in which one or more hollow interior 41 single-direction collapsible structures 43 are attached to form an interconnected structure, such as, e.g. illustrated in FIGS. 2 and 3, it may be sufficient that one or more apertures 42 be provided on only one of the single-direction collapsible structures 43 forming the interconnected structure, with the fluid communication between the hollow interiors 41 of the fluidly interconnected single-direction collapsible structures 43 allowing for the collapse or expansion of each of the interconnected single-direction collapsible structures 43 in response to a change in external pressure.

The one or more apertures 42 may be formed at any desired locations about the exterior surfaces of the single-direction collapsible structures 43, and the apertures 42 may be arranged, spaced, dimensioned, and shaped in any number of desired configurations. As will be understood, in some embodiments, the arrangement and placement of apertures 42 about the exterior of the single-direction collapsible structures 43 may depend on the arrangement of and/or the other layers incorporated into the wound dressing 100. For example, in embodiments in which the active layer 40 is arranged between an upper absorbent layer 30 and a lower wound interface layer 10 and/or embodiments in which the materials forming the various layers of the wound dressing 100 have no or limited porosity, the one or more apertures 42 may be formed about the outwardly facing ends of the single-direction collapsible structures 43, so as to minimize the risk that the apertures 42 become occluded during use.

As an alternative to providing apertures 42 about the exterior surfaces of hollow interior 41 single-direction collapsible structures 43, in some embodiments, one or more ports 49 may be formed about the exteriors of the surfaces of hollow interior 41 single-direction collapsible structures 43. The ports 49 may be configured to fluidly connect to the drive unit 70 (via, e.g. tubing 75). This direct connection between the hollow interior 41 of the single-direction collapsible structure 43 and the drive unit 70 may provide for a greater degree of control over the collapse and expansion of the single-direction collapsible structure 43.

As with the apertured single-direction collapsible structure 43 embodiments described above, each discrete, non-interconnected single-direction collapsible structure 43 may be provided with a port 49, whereas in embodiments in which one or more hollow interior 41 single-direction collapsible structures 43 are attached to form an interconnected structure it may be sufficient to provide only a single port 49 on one of the single-direction collapsible structures 43 forming the interconnected structure.

2. Multi-Direction Collapsible Structure

As illustrated in FIG. 5, in various embodiments, the one or more pneumatic members 45 of the active layer 40 may comprise one or more multi-direction collapsible structures 53 designed to collapse and expand in more than one direction in response to changes in pressure. In some embodiments, the multi-direction collapsible structure(s) 53 may be configured to collapse in both the longitudinal and lateral directions. In various embodiments, the multi-direction collapsible structure 53 may be made from a compressible material, such as an open-cell foam, and may define a plurality of pneumatic pathways 55 extending through the multi-direction collapsible structure 53 that interconnect to form a honeycomb-like structure.

The multi-direction collapsible structure 53 forming the active layer 40 may operate on principles similar to and in a manner like the operation of the wound interface layer 10 embodiments formed with through-holes 13 as described above. However, given the different purpose and role in the functioning of the wound dressing 100 that the multi-direction collapsible structure 53 plays as compared to embodiments of the wound interface layer 10 formed with through-holes 13, there are notable differences between the configuration and design of the multi-direction collapsible structure 53 of the active layer 40 and that of embodiments of the wound interface layer 10 formed with through-holes 13.

In configuring, sizing and arranging the through-holes 13 in the wound interface layer 10 embodiments described above, considerations must be made to balance the ability of the through-holes 13 to provide the desired degree of collapse of the wound-facing surface 11 of the wound interface layer 10 and the amount of surface area of the wound-facing surface 11 that is available to contact the tissue site 5 in order to achieve the desired degree of debris 7 disruption. In particular, incorporating larger dimensioned through-holes 13 in the wound interface layer 10 may come at the cost of decreasing the surface area of the wound-facing surface 11. Accordingly, even though the larger dimensioned through-holes 13 may allow for greater collapse of—and resultant lateral and/or longitudinal translation of—the wound-facing surface 11 relative to the tissue site 5, the limited surface area of the wound-facing surface 11 may restrict the amount of contact that the wound interface layer 10 may have with debris 7 at the tissue site 5. With more limited debris 7 contact, the degree to which the wound interface layer 10 may achieve desired tissue site 5 debridement may be limited.

On the other hand, attempting to maximize the surface area of the wound-facing surface 11 may come at the cost of decreasing the dimensions of the through-holes 13. Accordingly, even though the wound-facing surface 11 may have a surface area that provides a desired degree of contact with the tissue site 5, the limited ability of the though-holes 13 to collapse may result in the wound interface layer 10 not being translated laterally and/or longitudinally relative to the tissue site 5 by an amount sufficient to result in the desired debris 7 debridement.

In contrast, because the multi-direction collapsible structure 53 of the active layer 40 is not intended to be in contact with the tissue site 5, the configuration, sizing and arrangement of the pneumatic pathways 55 of the honeycomb-like multi-direction collapsible structure 53 need not be limited based on surface area considerations. Accordingly, the pneumatic pathways 55 of the multi-direction collapsible structure 53 may be configured, sized and arranged based on the degree and amount of wound interface layer 10 movement that is desired. In some embodiments, the only constraint on the size of the pneumatic pathways 55 may be ensuring that the walls separating adjacent pneumatic pathways 55 are not so small so as to be too fragile to sustain the application of pressure to the active layer 40.

Turning to FIG. 5, the multi-direction collapsible structure 53 may be constructed with a plurality of perforations or pneumatic pathways 55 extending entirely or partially through the multi-direction collapsible structure 53 from a lower surface 51 to an upper surface 52 of the multi-direction collapsible structure 53. The dimensions of the pneumatic pathways 55 may be varied as desired. While in some embodiments each of the pneumatic pathways 55 will have identical dimensions, in various embodiments, the pneumatic pathways 55 may be formed having varied dimensions.

Regardless of the dimensions selected for the pneumatic pathways 55, in embodiments in which the multi-direction collapsible structure 53 is formed from a foam-like or other porous material, it is to be understood that the pneumatic pathways 55 do not include the pores of the material forming the multi-direction collapsible structure 53, but rather are discrete perforations formed through the material forming the multi-direction collapsible structure 53.

The pneumatic pathways 55 may be arranged about the active layer 40 in any number of desired arrangements or patterns, including a random arrangement of the pneumatic pathways 55 about the multi-direction collapsible structure 53. As illustrated in FIG. 5, in some embodiments, the pneumatic pathways 55 may be arranged linearly, with adjacent rows of pneumatic pathways 55 optionally being offset from one another.

As shown in FIG. 5, in some embodiments, the pneumatic pathways 55 may have a hexagonal shape. In other embodiments, the pneumatic pathways 55 may define any number of, or any combination of, other shapes, including, e.g. circular, ovoid, or triangular shapes. When contracted, pneumatic pathways 55 having different cross-sectional shapes may collapse in different directions and by different distances. Given that the movement of the multi-direction collapsible structure 53 as the pneumatic pathways 55 collapse is adapted to translate and/or oscillate the wound interface layer 10, in various embodiments the cross-sectional shape of the pneumatic pathways 55 may be based on the degree, direction, and/or type of lateral and/or longitudinal movement of the wound interface layer 10 relative to the tissue site 5 that is desired.

Regardless of the shape, size, arrangement, or degree to which the pneumatic pathways 55 extend through the multi-direction collapsible structure 53, the pneumatic pathways 55 define voids in the multi-direction collapsible structure 53. In response to the multi-direction collapsible structure 53 being subjected to negative pressure, the voids provide spaces into which the multi-direction collapsible structure 53 is laterally and/or longitudinally collapsed. As the multi-direction collapsible structure 53 is compressed from its initial, relaxed configuration, the translation of the multi-direction collapsible structure 53 into the voids is transferred to the wound interface layer 10 to which the active layer 40 is attached, thereby driving the wound interface layer 10 in a desired manner.

b. Film Layer

In various embodiments, the active layer 40 may optionally include a film layer 60 to which the pneumatic members 45 may be mounted, laminated or otherwise attached or interconnected to. Additionally, in various embodiments, the film layer 60 may be used as the basis by which the pneumatic members 45 are affixed to the wound interface layer 10. Alternatively, in some embodiments, the film layer 60 may be omitted from active layer 40, with the pneumatic members 45 of the active layer 40 being attached directly to the wound interface layer 10.

The size and shape of the film layer 60 may be varied as desired. In various embodiments, the outer periphery of the film layer 60 may be shaped and sized to generally correspond to, or optionally be smaller than, the outer periphery of the wound interface layer 10.

The film layer 60 may be adapted to elastically deform upon application of a stretching force to the wound dressing 100. For example, in some embodiments, the film layer 60 may be designed to elastically stretch when a stretching force is applied and elastically recover when the stretching force is removed, such as, e.g. may occur as a result of the collapse and expansion of the pneumatic members 45 that are supported by film layer 60. In other words, film layer 60 may be configured to exhibit substantially elastic deformation and recovery.

Film layer 60 may be a thin layer made of any number of elastic materials. For example, film layer 60 may be a polyurethane film, a polyethylene film, or other thin elastic. In some embodiments, film layer 60 may be substantially impermeable to liquid and substantially permeable to moisture vapor.

As illustrated e.g. in FIGS. 2, 3 and 5, film layer 60 may optionally include one or more fenestrations 63 adapted to allow for the transfer of fluids and pressure to/from the wound interface layer 10. The fenestrations 63 may also be adapted to reduce the amount of force required to stretch film layer 60. In some embodiments, such as illustrated, e.g. in FIGS. 3 and 4, film layer 60 may comprise an upper film 61 and a lower film 62 that encapsulate the pneumatic members 45. In some such embodiments, such as illustrated in FIG. 3, one or both of the upper film 61 and the lower film 62 may include fenestrations 63, such that the interior 66 of the film layer 60 and the pneumatic members 45 encapsulated therein are in fluid communication with (and thereby subject to changes in the pressure of) the external environment.

Referring to FIG. 4, in other dual-film film layer 60 embodiments, both the upper film 61 and the lower film 62 may be formed without fenestrations 63, with the edges of the upper film 61 and lower film 62 being attached together to form a fluid-tight seal that isolates the interior 66 of the film layer 60 from the external environment. In such embodiments, the film layer 60 may comprise one or more outlets, such as e.g. a port 67, by which fluid communication may be established between the film layer 60 interior 66 and the external environment, and by which the pressure in the film layer 60 interior 66 may be controlled as desired.

In film layer 60 embodiments having a pneumatically isolated interior, such as, e.g. illustrated in FIG. 4, the film layer 60 may be dimensioned smaller than the wound interface layer 10, such that fluid and negative pressure may pass through to the wound interface layer 10. In other embodiments, one or more fenestrations 63 may extend through the portions of the upper film 61 and lower film 62 extending outwards from an outer periphery of the film layer 60 interior 66.

iii. Absorbent Layer

An absorbent layer 30 may optionally be coupled to the active layer 40 opposite the wound interface layer 10, such that the active layer 40 is encapsulated between the absorbent layer 30 and the wound interface layer 10. The absorbent layer 30 may act as a manifold that is adapted to collect and/or distribute fluid and/or pressure across a tissue site 5. For example, the absorbent layer 30 may be adapted to receive and distribute negative pressure across a tissue site 5 to which the wound dressing 100 is applied, allowing for the wicking of fluid (e.g. exudate) from the tissue site 5 and providing a distributed compressive force along the tissue site 5. As another example, the absorbent layer 30 may be used to facilitate the delivery of fluid across a tissue site 5.

In embodiments incorporating an absorbent layer 30, the size and shape of the absorbent layer 30 may be varied as desired. In various embodiments, the outer periphery of the absorbent layer 30 may be shaped and sized to generally correspond to, or optionally be smaller than, the outer periphery of the wound interface layer 10.

Any material or combination of materials might be used for the absorbent layer 30. In some embodiments, the absorbent layer 30 may comprise a porous and permeable foam layer, with the absorbent layer 30 being formed from a reticulated, open-cell polyurethane or polyether foam that allows good permeability of wound fluids while under a reduced pressure. In one non-limiting example, the absorbent layer 30 may be an open-cell, reticulated polyurethane foam such as GranuFoam® dressing available from Kinetic Concepts, Inc. of San Antonio, Tex. In other embodiments the absorbent layer 30 may be an open-cell, reticulated polyurethane foam such as a V.A.C. VeraFlo® foam, also available from Kinetic Concepts, Inc., of San Antonio, Tex. In yet other embodiments, the absorbent layer 30 may be formed of un-reticulated open-cell foam.

Drape Layer

A drape layer 20 adapted to seal to a patient's skin 3 may advantageously be provided to position and maintain the active debridement wound dressing 100 about the desired treatment tissue site 5. An attachment device, such as e.g. an adhesively coated margin 23 as illustrated in FIGS. 1 and 6, may be used to attach the drape layer 20 to a desired location along the patient's skin 3. In various embodiments, the drape layer 20 may provide a bacterial barrier and protection from physical trauma, and may be permeable to water vapor but impermeable to liquid.

Drape layer 20 may be formed from any number of materials, such as, e.g. polyurethane film. In some embodiments, the drape 20 may be adapted to provide a fluid-tight seal with the patient's skin 3 surrounding the tissue site 5 that is to be treated. In such embodiments, the drape layer 20 may be constructed from a material adapted to reduce evaporative losses and provide and maintain a fluid seal. As non-limiting examples, the drape layer 20 may be formed from materials that include a silicone, 3M Tegaderm® drape material, acrylic drape material such as one available from Avery, or an incise drape material.

Drive Unit

As explained above, the active layer 40 is designed to intentionally oscillate or translate the wound interface layer 10 in response to the collapse and expansion of the pneumatic members 45 forming the active layer 40. To that effect, wound debridement system 1 may include a drive unit 70 adapted to generate the required changes in pressure to achieve the desired movement of the wound interface layer 10. The drive unit 70 may comprise any number of or any combination of known devices adapted to generate and deliver negative and/or positive pressure.

The drive unit 70 may be directly or indirectly pneumatically coupled to the active layer 40 and is adapted to intermittently apply pressure to the active layer 40. In general, the drive unit 70 is adapted to apply pressure to collapse or expand the pneumatic members 45 from an initial configuration, following which the drive unit 70 is adapted to interrupt the application of pressure (or, in some embodiments, apply a second, opposite pressure is applied to counter the first applied pressure), thereby allowing the pneumatic members 45 to expand or collapse to their initial configuration.

The drive unit 70 may be incorporated into the wound debridement system 1 in any number of different forms. For example, in some embodiments, such as, e.g. illustrated in FIGS. 2B and 2C, the drive unit 70 may be formed within or on the wound dressing 100, while in other embodiments, such as, e.g. illustrated in FIG. 1, the drive unit 70 may be provided as a standalone device that is separate from the wound dressing 100.

i. Non-Localized Pressure Application

In various embodiments, such as e.g. illustrated in FIG. 6, the drive unit 70 may be used to control changes in the ambient environment in which the wound dressing 100 (including the active layer 40) is enclosed to indirectly activate the pneumatic members 45 of the active layer 40 and thereby drive the wound interface layer 10 in a lateral and/or longitudinal direction relative to the tissue site 5. In such embodiments, drape layer 20 may be adapted to define a sealed, substantially fluid-tight treatment space 25 between a lower surface of the drape layer 20 and the patient's skin 3. A fluid connection between the drive unit 70 and the treatment space 25 (via, e.g. tubing 75 attached to a port 28 attached to the drape layer 20) may allow for the pressure within the treatment space 25 to be varied by the drive unit 70.

In such embodiments, a desired activation (i.e. collapse and/or expansion) of the pneumatic members 45 and resultant lateral and/or longitudinal movement of the wound interface layer 10 relative to the tissue site 5 may be achieved by varying the type or amount of pressure that is delivered by the drive unit 70 to the treatment space 25. Because the delivery of pressure to drive the pneumatic members 45 is not localized to the active layer 40, in such embodiments the pressure applied by the drive unit 70 to drive the active layer 40 may also result in pressure being applied to the tissue site 5 that is located within the treatment space 25, with the pressure at the tissue site 5 being substantially equivalent to the pressure at the active layer 40. Accordingly, operation of such wound debridement system 1 embodiments may result not only in debridement of debris 7 at the tissue site 5, but may also advantageously provide benefits similar to or the same as those of NPWT treatments to the tissue site 5 in doing so.

ii. Isolated Pressure Application

In various embodiments, it may be desirable that the other components of the wound dressing 100 and/or the tissue site 5 to which the wound dressing 100 is applied not be subject to the same changes in pressure that the active layer 40 is subjected to during operation of the wound debridement system 1. Accordingly, in some embodiments, the active layer 40 may be pneumatically isolated from the rest of the wound dressing 100 such that the pressures that the pneumatic members 45 are subjected to by the drive unit 70 are not necessarily transmitted to the remaining portions of the wound dressing 100 and/or tissue site 5.

As illustrated in FIG. 1, in one embodiment, this isolation of the active layer 40, and in particular the pneumatic members 45 of the active layer 40, may be achieved by encapsulation of the pneumatic members 45 of the active layer 40 within the film layer 60. At least the portions of the upper film 61 and lower film 62 defining the hollow interior 66 of the film layer 60 within which the pneumatic members 45 are encapsulated are provided free of any fenestrations 63. Accordingly, pressure delivered by the drive unit 70 is applied directly to the pneumatic members 45 encapsulated by the film layer 60 and is localized to the interior 66 of the film layer 60. As such, in such embodiments, the pressure to which the active layer 40 is subjected to is not necessarily the same pressure as the pressure at the tissue site 5. As illustrated in FIG. 1, the pneumatic connection between the drive unit 70 and the interior 66 of the film layer 60 may be provided via a connection between tubing 75 and a port 67 extending through the film layer 60.

Although the embodiment described above (i.e. in which each of the pneumatic members 45 of the active layer 40 is encapsulated by the film layer 60) may allow for the isolated application of pressure to the active layer 40, each of the one or more pneumatic members 45 forming the active layer 40 are subjected to the same pressure. In particular, the pressure to which each pneumatic member 45 is subject is equal to the pressure that is applied to the interior 66 of the film layer 60 by the drive unit 70. However, in some embodiments, it may be desirable to use the drive unit 70 to apply different amounts and/or types of pressure to achieve individualized and independent activation and control of the one or more pneumatic members 45 forming the active layer 40.

Accordingly, in some embodiments, the one or more of the pneumatic members 45 forming the active layer 40 may be individually encapsulated (e.g. by the film layer 60) such that each encapsulated pneumatic member 45 is pneumatically isolated from the other pneumatic members 45 forming the active layer 40. A fluid connection between the drive unit 70 and the individually pneumatic members 45 may allow the drive unit 70 to selectively collapse and expand each of the pneumatic members 45 independently from the activation (i.e. collapse and expansion) of the remaining pneumatic members 45 forming the active layer 40.

As illustrated in FIGS. 2B and 2C, in embodiments in which the pneumatic members 45 comprise one or more non-apertured single-direction collapsible structures 43 having hollow interiors 41, the pneumatic isolation of the pneumatic members 45 may be achieved by establishing a fluid connection between the hollow interiors 41 of the non-apertured single-direction collapsible structures 43 and the drive unit 70. As shown in FIGS. 2B and 2C, in some embodiments, this fluid connection may be provided via a connection of the drive unit 70 to a port 49 formed on the single-direction collapsible structure 43. This fluid, pneumatic connection between the drive unit 70 and the port 49 of the single-direction collapsible structure 43 may allow for the isolated control of the single-direction collapsible structure 43 to which the drive unit 70 is coupled.

As will be understood, in embodiments in which the drive unit 70 is pneumatically connected to the hollow interior(s) 41 of one or more non-apertured single-direction collapsible structures 43, the interconnectedness of the hollow interiors 41 of a non-apertured single-direction collapsible structures 43 forming the active layer 40 may allow for the independent control of one or more single-direction collapsible structures 43. For example, where the hollow interiors 41 of the one or more non-apertured, single-direction collapsible structures 43 are fluidly connected, a connection between the drive unit 70 and a port 49 on a single one of the interconnected single-direction collapsible structures 43 may allow the drive unit 70 to activate each of the interconnected single-direction collapsible structures 43. Accordingly, in the embodiment of FIGS. 2A-2C, where the hollow interiors 41 each of the bellowed limbs 43 and the hub 48 of the spoke-like pneumatic member 45 are fluidly connected, pressure applied to the hub 48 by the drive unit 70 may be transferred amongst the bellowed limbs, resulting in the desired collapse and expansion of the active layer 40.

In contrast, in embodiments in which the hollow interiors 41 of non-apertured singled-direction collapsible structures 43 are pneumatically isolated from one another, each of the single-direction collapsible structures 43 may be controlled independent from one another. In such embodiments, the selective pneumatic attachment of the drive unit 70 to particular pneumatic members 45 and the selective delivery of pressure by the drive unit 70 to these particular pneumatic members 45 may allow the drive unit 70 to provide multiphasic, multi-directional oscillation and/or translation of the active layer 40.

For example, in one embodiment (not shown), the active layer 40 may comprise a pneumatic member 45 formed of a plurality of laterally extending pneumatic members 45 and a plurality of longitudinally extending pneumatic members 45 that form a grid-like pattern. The drive unit 70 may be operably connected to at least one of the laterally extending pneumatic members 45 and at least one of the longitudinally extending pneumatic members 45. By selectively varying the delivery or negative or positive pressure to the laterally and/or longitudinally extending pneumatic members 45, the drive unit 70 may be adapted to allow for activation of the active layer 40 is such a manner that allows for both lateral and/or longitudinal translation of the wound interface layer 10 relative to the tissue site 5.

Control Unit

In various embodiments, the delivery of pressure by the drive unit 70 to the active layer 40 to collapse or expand the pneumatic members 45 of the active layer 40 may be based upon signals received from an optionally included control unit 80. In some embodiments, the control unit 80 may communicate with the drive unit 70 using any number of known communication methods, including wireless communication.

The control unit 80 may be adapted to vary the type and amount of pressure that is to be delivered by the drive unit 70 based on any number of factors including, but not limited to: the tissue site 5 being treated (such as, but not limited to bone tissue, adipose tissue, muscle tissue, neural tissue, dermal tissue, vascular tissue, connective tissue, cartilage, tendons, or ligaments, chronic, acute, traumatic, subacute, and dehisced wounds, partial-thickness burns, ulcers, flaps, grafts, etc.); the type of debris 7 being debrided (such as, but not limited to necrotic tissue, eschar, impaired tissue, other sources of infection, exudate, slough including hyperkeratosis, pus, foreign bodies, biofilm, or other types of bioburden, etc.); the thickness, consistency, color and/or moisture levels of the debris 7; the desired relative amount of lateral and/or longitudinal movement of the wound interface layer 10 relative to the tissue site 5; etc. In some embodiments the control unit 80 and drive unit 70 may be formed as a single unit, while in other embodiments the drive unit 70 and control unit 80 may be provided separately.

Use with Other Treatment Systems

As illustrated by the embodiment of FIG. 1, in various embodiments, wound debridement system 1 may be used as a standalone therapy device, with drive unit 70 and optional control unit 80 being provided solely for the operation of the wound debridement system 1. However, as noted previously, in other embodiments it may be possible to utilize the wound debridement system 1 in conjunction with one or more additional therapeutic treatment systems configured to provide a desired therapeutic treatment to the tissue site 5 in addition to the debris 7 debridement provided by the wound debridement system 1.

In embodiments in which the wound debridement system 1 is used in conjunction with one or more additional therapeutic treatment systems, one or more of the components of the wound debridement system 1 may optionally comprise one or more elements of the additional therapeutic treatment system. For example, the drape layer 20 may optionally be omitted from the wound dressing 100 in embodiments in which the wound debridement system 1 is used in conjunction with an additional therapeutic treatment system incorporating a backing layer to position and maintain an element of the additional therapeutic treatment system against a patient's skin 3 during therapy. Accordingly, as illustrated e.g. by FIG. 6, in embodiments in which the additional therapeutic treatment system is a NPWT system 200, the backing layer 220 of the NPWT system 200 that is sealed to a patient's skin 3 may optionally also serve as the drape layer 20 of the wound debridement system 1.

Similarly, in some embodiments the drive unit 70 may comprise a pressure source included as a part of an additional therapeutic treatment system that the wound debridement system 1 is used in conjunction with. In some such embodiments, the pressure source of the additional therapeutic treatment system may be adapted to independently regulate and deliver pressure to a plurality of devices, such that the pressure source may allow the drive unit 70 to deliver pressure to the wound dressing 100 independently from the pressure that is delivered by the pressure source to the additional therapeutic treatment system. For example, as illustrated in FIG. 6, the pump 270 of the NPWT system 200 may also serve as the drive unit 70.

In other embodiments, the pressure source of the additional therapeutic treatment system may not be adapted to allow for independent regulation and delivery of pressure to a plurality of devices, with the operation of the drive unit 70 being dependent on the pressure that is delivered by the pressure source to the additional therapeutic treatment system.

In some embodiments, the wound debridement system 1 may be used in conjunction with (either before, during or after) existing tissue removal and debridement systems and methods. For example, the wound debridement system 1 may be used prior to enzymatic debridement to soften the debris 7. In another example, an existing mechanical debridement technique or method may be used to remove a portion of the debris 7 at the tissue site 5, and the wound debridement system 1 may then be used to remove the remaining debris 7 while reducing the risk of trauma to the tissue site 5.

As illustrated in FIG. 6, in various embodiments, the additional therapeutic treatment system that the wound debridement system 1 is used in conjunction with may be a NPWT system 200. The use of the wound debridement system 1 with the NPWT system 200 may improve the functioning of both the systems, as the debridement of the debris 7 at the tissue site 5 may improve the efficacy of the NPWT treatment of the tissue site 5, while the negative pressure applied by the NPWT system 200 may advantageously assist in removing the debris 7 that has been loosened and removed from the tissue site 5 by the wound debridement system 1.

In some embodiments in which the wound debridement system 1 is used in conjunction with a NPWT system, the rigidity of the materials used in the active layer 40 of the wound dressing 100 and the rate of the intermittent application of negative pressure used to drive the active layer 40 may be selected to ensure that the intermittent release of negative pressure utilized to drive the active layer 40 does not interfere with the continuous, uninterrupted application of negative pressure by the NPWT system.

In particular, the pneumatic members 45 of the active layer 40 may be constructed such that the activation (i.e. collapse) of the pneumatic members 45 will not occur until a predetermined threshold pressure is reached, with the predetermined threshold pressure being a negative pressure that is greater than the negative pressure applied as part of the NPWT treatment. The activation of the pneumatic members 45 can then be controlled by intermittently ramping up the negative pressure within the treatment space 25 from an initial negative pressured applied as part of the NPWT treatment to the predetermined threshold level, and subsequently decreasing the negative pressure to the initial, negative pressure level.

By configuring the active layer 40 such that the threshold pressure required to collapse the active layer 40 is greater than the negative pressure applied as part of the NPWT treatment, the wound debridement system 1 allows for the continuous driving of the wound interface layer 10 by the active layer 40, even when the NPWT system is sustaining a negative pressure within the treatment space 25. Also, because the activation of the pneumatic members 45 is based on the cyclical variation of pressure from a first negative pressure (i.e. the NPWT treatment pressure) to a second, greater pressure (threshold pressure), operating the pump 270 of the NPWT system on an intermittent cycle in which the pressure applied by the pump 270 is cycled between the first and second pressure will allow the pump 270 of the NPWT system to control both the NPWT treatment and the wound debridement.

Alternatively, in some embodiments in which the wound debridement system 1 is used in conjunction with a NPWT system 1, such as e.g. illustrated in FIG. 6, the risk of interfering with the continuous negative pressure that is applied during NPWT treatment may be entirely avoided by pneumatically isolating the pneumatic members 45. In such embodiments, the pneumatic members 45 can be driven independently from the pressure at the tissue site 5 that is imparted by the NPWT system 200.

In some embodiments, the wound debridement system 1 may be used in conjunction with an instillation therapy system. In such embodiments, a NPWT system may also optionally be included. The instillation therapy system may assist in the hydration and flushing of the tissue site 5, which may facilitate the debridement of the debris 7 by the wound debridement system 1. In turn, the wound debridement system 1 may allow for greater control of the instillation therapy system.

More specifically, in some embodiments, the active layer 40 may be actuated by the drive unit 70 during the instillation fill, soak and removal phases of instillation therapy. During the fill phase, the actuation of the active layer 40 may encourage a thorough and uniform distribution of the instillation fluid at the tissue site 5 by the wound interface layer 10. During the soak phase, the hydrating effect of the instillation fluid at the tissue site 5 may increase the debridement efficiency of wound interface layer 10. Additionally, in some embodiments, the instillation fluid may optionally contain a topical solution that may assist in reducing patient discomfort during the debridement process. Finally, the flushing and fluid removal phase of the instillation therapy may encourage and assist in the removal of debrided debris 7 from the tissue site 5.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

We claim:

1. An active debridement wound dressing comprising:
   a wound interface layer comprising an abrasive surface configured to contact a wound and mechanically debride the wound when the wound interface layer moves relative to the wound; and
   an active layer coupled to the wound interface layer and comprising:
      a fenestrated film fixed to the wound interface layer; and
      a pneumatic structure comprising a plurality of pneumatic segments fixed to the fenestrated film, the pneumatic structure configured to expand and collapse responsive to a pneumatic pressure applied to the active layer, thereby causing the wound interface layer to move relative to the wound and mechanically debride the wound.

2. The active debridement wound dressing of claim 1, wherein the pneumatic structure further comprises:
   a central pneumatic hub; and
   the plurality of pneumatic segments comprise a plurality of radial segments extending radially outward from the central hub.

3. The active debridement wound dressing of claim 1, further comprising:
   a first encapsulation layer located on a first side of the active layer between the active layer and the wound interface layer; and
   a second encapsulation layer located on a second side of the active layer opposite the wound interface layer;
   wherein the first encapsulation layer and the second encapsulation layer encapsulate the active layer and pneumatically isolate the active layer from the wound.

4. The active debridement wound dressing of claim 1, further comprising a control unit coupled to the active layer and configured apply a positive or negative pneumatic pressure to the active layer.

5. The active debridement wound dressing of claim 4, wherein the control unit is configured to communicate with a driver unit outside the wound dressing and to apply the pneumatic pressure to the active layer upon receiving a control signal from the driver unit.

6. The active debridement wound dressing of claim 1, wherein the pneumatic structure is configured to oscillate between an expanded size or shape and a collapsed size or shape to impart oscillating movement to the wound interface layer.

7. An active debridement wound therapy system comprising:
   a wound dressing comprising:
      a wound interface layer comprising an abrasive surface configured to contact a wound and mechanically debride the wound when the wound interface layer moves relative to the wound; and
      an active layer coupled to the wound interface layer and comprising a pneumatic structure having a central pneumatic hub and a plurality of radial segments extending radially outward from the central hub, the pneumatic structure configured to expand and collapse responsive to a pneumatic pressure applied to the active layer, thereby causing the wound interface layer to move relative to the wound and mechanically debride the wound; and
   a therapy unit separate from the wound dressing and configured to cause the pneumatic pressure to be applied to the active layer.

8. The active debridement wound therapy system of claim 7, wherein the wound dressing comprises a control unit coupled to the active layer and configured to communicate with the therapy unit;
   wherein the control unit is configured to apply the pneumatic pressure to the active layer upon receiving a control signal from the therapy unit.

9. The active debridement wound therapy system of claim 7, the wound dressing further comprising:
   a first encapsulation layer located on a first side of the active layer between the active layer and the wound interface layer; and
   a second encapsulation layer located on a second side of the active layer opposite the wound interface layer;
   wherein the first encapsulation layer and the second encapsulation layer encapsulate the active layer and pneumatically isolate the active layer from the wound.

10. The active debridement wound therapy system of claim 7, wherein the pneumatic structure is configured to collapse upon application of negative pressure to the active layer and return to a non-collapsed size or shape when the negative pressure is removed.

11. The active debridement wound therapy system of claim 7, wherein the pneumatic structure is configured to expand upon application of positive pressure to the active layer and return to a non-expanded size or shape when the positive pressure is removed.

12. The active debridement wound therapy system of claim 7, wherein the pneumatic structure is configured to oscillate between an expanded size or shape and a collapsed size or shape to impart oscillating movement to the wound interface layer.

* * * * *